United States Patent [19]
Boss et al.

[11] Patent Number: 6,028,666
[45] Date of Patent: Feb. 22, 2000

[54] FIBER OPTIC RAMAN SENSOR

[75] Inventors: Pamela A. Boss, San Diego; Stephen H. Lieberman, La Mesa, both of Calif.

[73] Assignee: The United States of America as represented by the Secretary of the Navy, Washington, D.C.

[21] Appl. No.: 09/197,319

[22] Filed: Nov. 19, 1998

[51] Int. Cl.$^7$ ............................... G01J 3/44; G01N 21/65
[52] U.S. Cl. ................................................... 356/301
[58] Field of Search ............................ 356/301; 385/12

[56] References Cited

U.S. PATENT DOCUMENTS

| | | |
|---|---|---|
| 4,573,761 | 3/1986 | McLachlan et al. . |
| 4,676,639 | 6/1987 | Van Wagenen . |
| 4,768,879 | 9/1988 | McLachlan et al. . |
| 4,802,761 | 2/1989 | Bowen et al. . |
| 5,144,374 | 9/1992 | Grego . |
| 5,194,913 | 3/1993 | Myrick et al. . |
| 5,247,343 | 9/1993 | Burch . |
| 5,261,410 | 11/1993 | Alfano et al. . |
| 5,401,959 | 3/1995 | Berkcan .............................. 250/227.23 |
| 5,404,218 | 4/1995 | Nave et al. . |
| 5,455,673 | 10/1995 | Alsmeyer et al. . |
| 5,774,610 | 6/1998 | O'Rourke et al. ......................... 385/12 |
| 5,842,995 | 12/1998 | Mahadevan-Jansen et al. ....... 356/301 |
| 5,911,017 | 6/1999 | Wach et al. ............................. 356/301 |

*Primary Examiner*—F. L. Evans
*Attorney, Agent, or Firm*—Harvey Fendelman; Michael A. Kagan; Eric James Whitesell

[57] ABSTRACT

An improved fiber optic Raman sensor (FORS) provides high sensitivity and effective rejection of Rayleigh backscatter and background Raman emissions. Multiple receiving optical fibers are arranged around a transmitting optical fiber to increase the sensitivity of the sensor to Raman emissions from an analysis sample. A Raman emission filter is coupled to the transmitting fiber for preventing output of Raman emissions from the optical fiber to the sample, and a Rayleigh line filter is coupled to the receiving optical fibers for removing Rayleigh line energy emitted by the analysis sample. Rayleigh backscatter emitted by the analysis sample is reduced by orienting the sensor at an appropriate angle with respect to the surface of the sample.

10 Claims, 3 Drawing Sheets

FIBER OPTIC RAMAN SENSOR

LICENSING INFORMATION

The invention described below is assigned to the United States Government and is available for licensing commercially. Technical and licensing inquiries may be directed to Harvey Fendelman, Legal Counsel For Patents, SPAWAR-SYSCEN SAN DIEGO CODE D0012 Room 103, 53560 Hull Street, San Diego, Calif. 92152-5001; telephone no. (619)553-3001; fax no. (619)553-3821.

BACKGROUND OF THE INVENTION

The present invention relates to detection of subsoil contaminants including chlorinated hydrocarbons. More specifically, but without limitation thereto, the present invention relates to a fiber optic probe for detecting Raman emissions that may be used with a cone penetrometer.

Raman spectroscopy is an emission technique that uses scattering of incident optical energy to produce spectral peaks that are frequency shifted from the incident optical energy. These so-called Raman emissions are believed to arise from changes in molecule polarization. Virtually all organic molecules display a characteristic Raman emission. The inherently high resolution of Raman spectra often permits the analysis of several chemicals present together in a mixture. This technique is particularly applicable to detecting chlorinated hydrocarbons that frequently contaminate subsoil around aquafers. Cone penetrometers have been used with a variety of probe designs to detect these contaminants.

The advent of inexpensive, portable Raman spectrometers has gained renewed interest in the area of Raman spectrometry. These spectrometers offer a minimum of components compared to conventional instrumentation and provide high light throughputs.

Despite the advantages of Raman spectroscopy and the technological advances, there are additional issues that must be resolved to realize a practical fiber optic Raman sensor (FORS), such as low sensitivity and interference from Raman emissions in the optical fibers.

A need therefore exists for a fiber optic Raman sensor that suppresses interference from the optical fibers, is operable with optical fiber lengths in excess of 30 meters, has high sensitivity, and is rugged enough to be deployed in a cone penetrometer.

SUMMARY OF THE INVENTION

An improved fiber optic Raman sensor of the present invention is directed to overcoming the problems described above, and may provide further related advantages. No embodiment of the present invention described herein shall preclude other embodiments or advantages that may exist or become obvious to those skilled in the art.

An improved fiber optic Raman sensor (FORS) of the present invention provides high sensitivity and effective rejection of Rayleigh backscatter and background Raman emissions. Multiple receiving optical fibers are arranged around a transmitting optical fiber to increase the sensitivity of the sensor to Raman emissions from an analysis sample. A Raman emission filter is coupled to the transmitting fiber for preventing output of Raman emissions from the optical fiber to the sample, and a Rayleigh line filter is coupled to the receiving optical fibers for removing Rayleigh line energy emitted by the analysis sample. Rayleigh backscatter emitted by the analysis sample is reduced by orienting the sensor at an appropriate angle with respect to the surface of the sample.

An advantage of the fiber optic Raman sensor of the present invention is that low level Raman emissions may be detected from samples with improved sensitivity.

Another advantage is that interference from optical fiber emissions is substantially reduced.

Yet another advantage is that the fiber optic Raman sensor of the present invention may be operated with optical fiber lengths in excess of 30 meters.

Still another advantage is that the fiber optic Raman sensor of the present invention can withstand the shock and vibration associated with operation in a cone penetrometer for detecting subsurface contaminants such as chlorinated hydrocarbons.

The features and advantages summarized above in addition to other aspects of the present invention will become more apparent from the description, presented in conjunction with the following drawings.

DESCRIPTION OF THE INVENTION

The following description is presented solely for the purpose of disclosing how the present invention may be made and used. The scope of the invention is defined by the claims.

Figure 1:
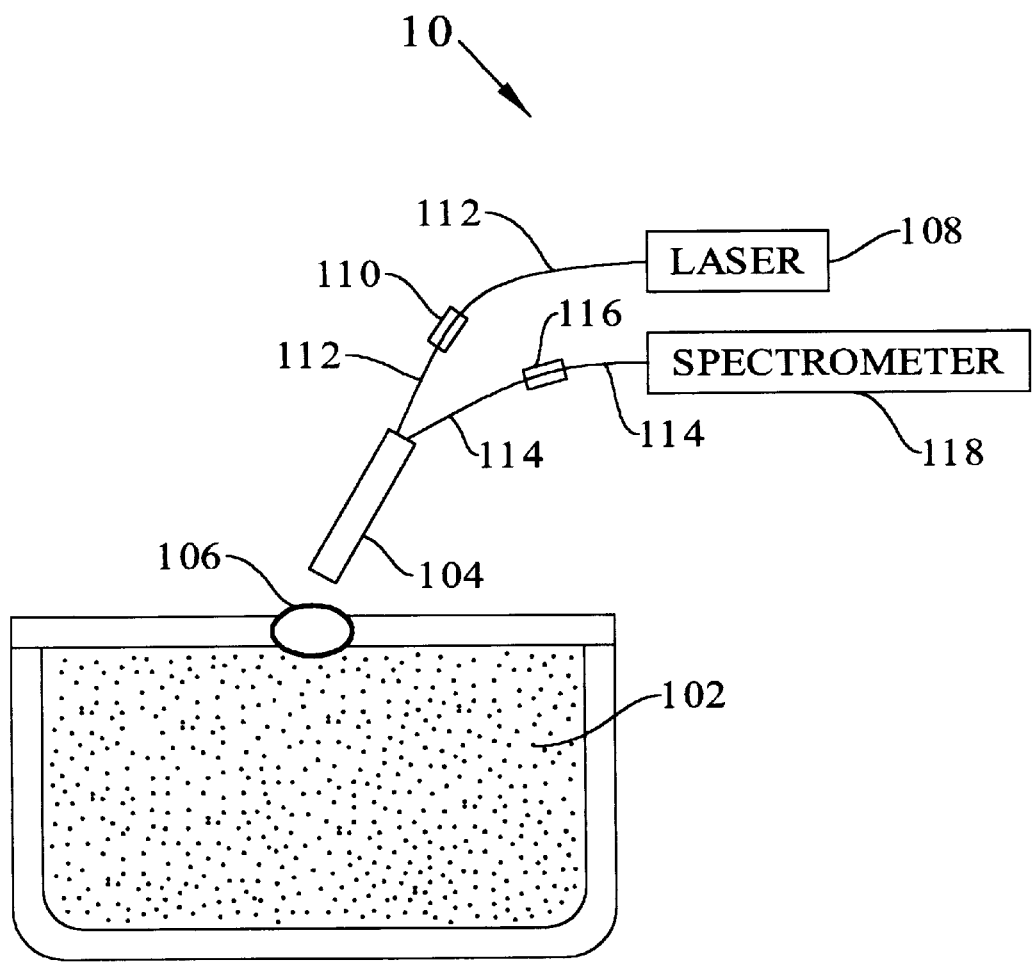
FIG. 1 is a diagram of a fiber optic Raman sensor (FORS) of the present invention.

FIG. 1 is a diagram of a fiber optic Raman sensor 10 of the present invention. A test sample 102 of, for example, subsurface soil, is maintained at a fixed distance and angle from fiber optic Raman sensor (FORS) probe tip 302 by a window 106. FORS probe tip 302 conducts excitation energy from laser source 108 through a transmitting optical fiber 112 and optical fiber Raman emission filter 110 to test sample 102. Raman emissions received from sample 102 by FORS probe tip 302 are conducted through a receiving optical fiber 114 through a Rayleigh line filter 116 to a spectrometer 118.

Laser source 108 may be, for example, an American Laser model 905 2.5 W tunable argon ion laser. Transmitting optical fiber 112 may be, for example, a single 365 $\mu$m diameter silica clad UV/VIS optical fiber. Receiving optical fiber 114 may have the same composition and diameter as transmitting optical fiber 112. Window 106 is preferably made of a material such as sapphire or diamond that is substantially transparent to Raman emissions and resists scratching from test sample 102. Spectrometer 118 may be, for example, a Chromex Raman One imaging system with a Princeton Instruments model TE/CCD-1153EM charge-coupled device detector and a model ST-130 controller. A Kaiser Optical Systems model P/N HNF-488-1.0 holographic notch filter may be included to reject the Rayleigh line from receiving optical fiber 114.

Figure 2:
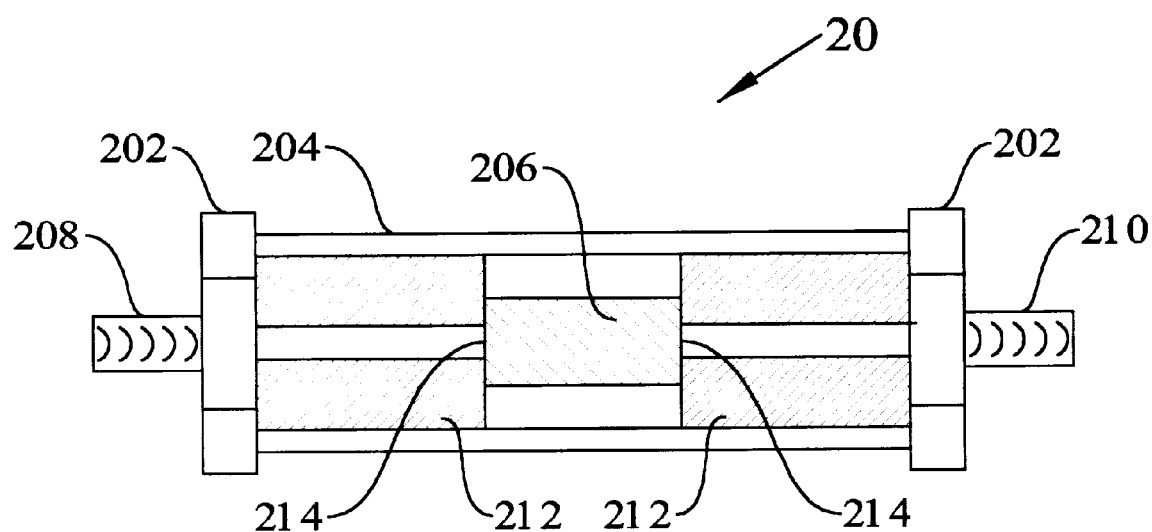
FIG. 2 is a diagram of an optical micro-filter.

FIG. 2 is a diagram of a micro-filter 20 that may be used for Raman emission filter 110 and Rayleigh line filter 116. SMA connectors 202 connect the optical fiber to micro-filter casing 204. Filter element 206 may be a bandpass element for Raman emission filter 110 or a longpass element for Rayleigh line filter 116. Filter element 206 preferably has a thickness of about 0.5 mm, which is substantially less then typical optical filters that require collimating graded index lenses to collimate the diverging beam emitted by the input optical fiber 208. The low thickness of filter element 206 results in lower optical energy loss from input optical fiber 208 to output optical fiber 210 than would result from a standard filter element thickness using collimating lenses. The optical efficiency of micro-filter 20 may be further increased by filling the air space between the ends 214 of optical fibers 208 and 210 with an index matching gel 212 to reduce reflective losses.

Figure 3:
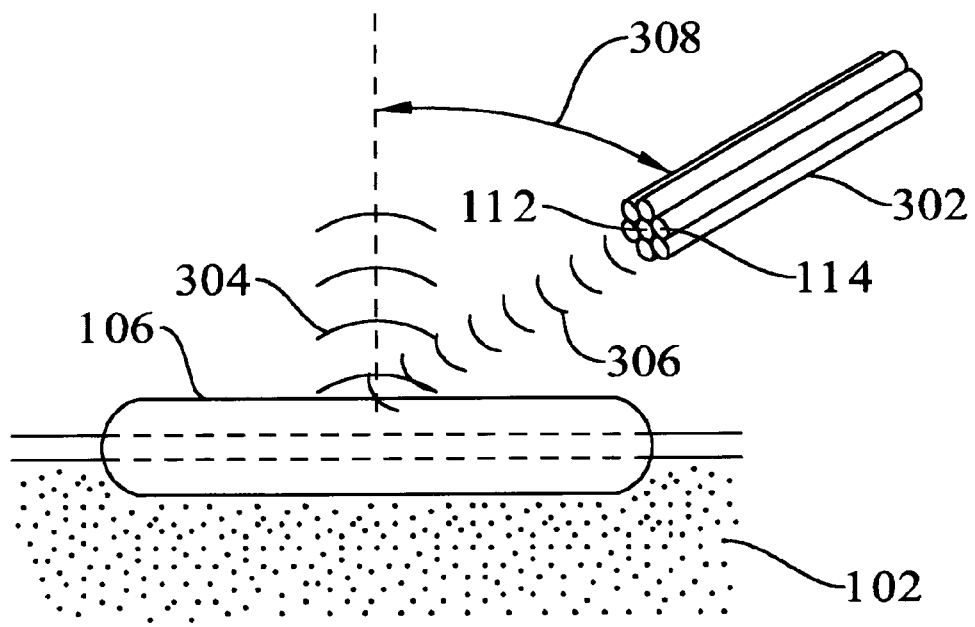
FIG. 3 is a magnified view illustrating the arrangement of the tip of the FORS probe of FIG. 1.

FIG. 3 is a magnified view illustrating the arrangement of probe tip 302 of FORS probe 10 in FIG. 1. Transmitting optical fiber 112 is arranged in the center of multiple receiving optical fibers 114 to collect Raman emissions 304 from sample 102 in response to excitation energy 306. FORS probe tip 302 is mounted at an angle 308 to reduce the reception of Rayleigh backscatter energy emitted by test sample 102. Angle 308 is preferably about 14 degrees from perpendicular to window 106.

Other modifications, variations, and applications of the present invention may be made in accordance with the above teachings other than as specifically described to practice the invention within the scope of the following claims.

We claim:

1. A fiber optic Raman spectroscopy probe comprising:

a transmitting optical fiber for conducting excitation energy from an excitation source to a test sample;

a Raman emission filter coupled to the transmitting optical fiber for preventing conduction of Raman emissions from the transmitting optical fiber to the test sample;

multiple receiving optical fibers arranged around the transmitting optical fiber for conducting Raman emissions from the test sample to an optical energy detector;

a Rayleigh line filter coupled to the receiving optical fibers for preventing conduction of Rayleigh line energy from the test sample to the optical energy detector;

and a sapphire window coupled to the receiving optical fibers at an appropriate collection angle for reducing conduction of fluorescence interference and Rayleigh backscatter energy from the test sample to the receiving optical fibers, wherein each filter comprises a micro-filter casing for coupling micro-filter elements to the optical fibers.

2. The fiber optic Raman spectroscopy probe of claim 1 wherein the Raman emission filter comprises a bandpass micro-filter having a filter element thickness sufficiently low to provide a greater optical efficiency than that provided by collimating the excitation energy through a filter element having a greater thickness with a collimating lens.

3. The fiber optic Raman spectroscopy probe of claim 2 wherein the bandpass micro-filter has a thickness less than or equal to about 0.5 mm.

4. The fiber optic Raman spectroscopy probe of claim 1 wherein the Rayleigh line filter comprises a longpass micro-filter having a filter element thickness sufficiently low to provide a greater optical efficiency than that provided by collimating the Raman emissions through a filter element having a greater thickness with a collimating lens.

5. The fiber optic Raman spectroscopy probe of claim 4 wherein the longpass micro-filter has a thickness less than or equal to about 0.5 mm.

6. The fiber optic Raman spectroscopy probe of claim 2 wherein the bandpass filter is coupled to the transmitting optical fiber by an index matching gel.

7. The fiber optic Raman spectroscopy probe of claim 4 wherein the longpass filter is coupled to the receiving optical fiber by an index matching gel.

8. The fiber optic Raman spectroscopy probe of claim 1 wherein the collection angle is about 14 degrees.

9. The fiber optic Raman spectroscopy probe of claim 1 further including the excitation source.

10. The fiber optic Raman spectroscopy probe of claim 9 wherein the excitation source is an argon ion laser.

* * * * *